(12) United States Patent
Goodman et al.

(10) Patent No.: US 6,413,496 B1
(45) Date of Patent: Jul. 2, 2002

(54) PHARMACEUTICAL COMPOSITIONS AND DEVICES FOR THEIR ADMINISTRATION

(75) Inventors: Michael Goodman, Ampthill (GB); Ake Lindahl, Skurup (SE)

(73) Assignee: Biogland Ireland (R&D) Limited, Dublin (IE)

( * ) Notice: Subject to any disclaimer, the term of this patent is extended or adjusted under 35 U.S.C. 154(b) by 0 days.

(21) Appl. No.: 09/325,927

(22) Filed: Jun. 4, 1999

Related U.S. Application Data

(63) Continuation-in-part of application No. 08/913,226, filed on Sep. 9, 1997, now abandoned, which is a continuation-in-part of application No. PCT/GB97/03360, filed on Dec. 4, 1997.

(30) Foreign Application Priority Data

Dec. 4, 1996 (GB) ............................................. 9625171
Dec. 20, 1996 (GB) ............................................. 9626449

(51) Int. Cl.$^7$ ............................................. A61K 9/12
(52) U.S. Cl. ......................... 424/45; 424/46; 514/509; 514/958; 128/203.15
(58) Field of Search ..................... 424/45, 46; 514/509, 514/958; 128/203.15

(56) References Cited

U.S. PATENT DOCUMENTS

| | | | |
|---|---|---|---|
| 3,608,781 A | | 9/1971 | Flynn |
| 5,186,925 A | | 2/1993 | Cholcha |
| 5,190,029 A | | 3/1993 | Byron et al. |
| 5,290,539 A | * | 3/1994 | Marecki |
| 5,474,758 A | | 12/1995 | Kwon |
| 5,508,023 A | | 4/1996 | Byron et al. |
| 5,607,662 A | | 3/1997 | Baskeyfield et al. |
| 5,653,961 A | | 8/1997 | McNally et al. |
| 5,658,549 A | * | 8/1997 | Akehurst et al. |
| 5,674,473 A | | 10/1997 | Purewal et al. |
| 5,683,677 A | * | 11/1997 | Purewal et al. |
| 5,775,321 A | | 7/1998 | Alband |
| 5,776,432 A | * | 7/1998 | Schultz et al. |
| 5,980,867 A | | 11/1999 | Tzou et al. |
| 6,143,277 A | * | 11/2000 | Ashurst |

FOREIGN PATENT DOCUMENTS

| | | |
|---|---|---|
| DE | 32 46 081 | 6/1984 |
| DE | 40 38 203 | 6/1992 |
| EP | 0 143 577 | 6/1985 |
| EP | 0 234 500 | 9/1987 |
| EP | 0 342 269 | 11/1989 |
| EP | 0342269 | 11/1989 |
| EP | 0 461 505 | 12/1991 |
| EP | 0 471 468 | 2/1992 |
| EP | 0 518 601 | 12/1992 |
| EP | 0 626 173 | 11/1994 |
| GB | 970027 | 9/1964 |
| WO | 92/14444 | 9/1992 |
| WO | 93/11747 | 6/1993 |
| WO | 96/32345 | 10/1996 |
| WO | 97/09034 | 3/1997 |

* cited by examiner

*Primary Examiner*—Raj Bawa
(74) *Attorney, Agent, or Firm*—Ropes & Gray

(57) ABSTRACT

A device for providing pharmaceutical doses comprising a container, filled with a pharmaceutical composition including a pharmaceutically active agent in a solution of liquified 1,1,1,2-tetrafluoroethane (HFC-134*a*), or 1,1,1,2,3,3,3 heptafluoropropane (HFC-227) and a carrier. The carrier can be a pharmaceutically acceptable alcohol, polyol, (poly)alkoxy derivative, fatty acid alkyl ester, polyalkylene glycol, or dimethyl sulphoxide. The device includes a valve arranged for delivering aerosol doses of said pharmaceutical composition to the exterior of the container, and at least a portion of the device is formed from a polyester.

59 Claims, 1 Drawing Sheet

PHARMACEUTICAL COMPOSITIONS AND DEVICES FOR THEIR ADMINISTRATION

CROSS-REFERENCE TO RELATED APPLICATIONS

This application is a continuation-in-part of U.S. application Ser. No. 08/913,226, filed Sep. 9, 1997, and now abandoned and a continuation-in-part of International Application No. PCT/GB97/03360, filed Dec. 4, 1997.

BACKGROUND OF THE INVENTION

The present invention relates to pharmaceutical compositions comprising a pharmaceutically active agent in liquified 1.1.1.2-tetrafluoroethane (HFC-134a) or 1,1,1,2,3,3,3-heptafluoropropane (HFC-227) as a propellant, for delivery in aerosol form, and to a device for delivering such a composition as an aerosol.

Most current aerosol spray formulations use one or more chlorofluorocarbon as a propellant; dichlorodifluoromethane being commonly used. However, chlorofluorocarbons have been implicated in the depletion of the ozone layer and their production, therefore, is being phased out. It has been found that certain hydrofluorocarbons, which are both of low toxicity and of suitable vapour pressure for use as aerosol propellants, are significantly less harmful to the ozone layer. Among such hydrofluorocarbons, 1,1,1,2-tetrafluoroethane (HFC-134a) and 1,1,1,2,3,3,3-heptafluoropropane (HFC-227) have been proposed as suitable propellants for pharmaceutical aerosols.

SUMMARY OF THE INVENTION

It has now been found that HFC-134a and HFC-227 can be used in combination with many pharmaceutically active agents, without causing any degradation to them or reducing their physiological activity.

Devices for administering metered aerosol doses of pharmaceutical preparations are well known in the art. Such devices include those disclose in WO 92/11190, U.S. Pat. No. 4,819,834 and U.S. Pat. No. 4,407,481. Many of these devices include metering valves having components formed from plastic materials, such as the valves available from Bespak PLC of Bergen Way, Kings Lynn, Norfolk PE30 2JJ, United Kingdom, in which the valve core, metering chamber and some other structural components are formed from plastic materials. The plastic materials currently used for forming these structural parts in valves employed with many chlorofluorocarbon containing formulations include certain acetal co-polymers.

Although the plastics employed to manufacture metering valves, including the aforementioned acetal co-polymers, have also been found to be stable in the presence of HFC-134a alone, the applicants, to their surprise, have determined that many of these plastics materials can be caused to swell in the presence of formulations which include certain carriers or active agent solubilizing co-solvents with HFC-134a. When such swelling takes place in a valve, the fit of mutually slidable components, such as metering chambers and valve cores, is adversely affected and they can bind together or become loose, causing the valve to leak or cease functioning altogether.

This problem has now been solved in accordance with a first aspect of the invention by a device for providing pharmaceutical doses comprising a container, filled with a pharmaceutical composition including a pharmaceutically active agent in a solution of liquified HFC-134a, or HFC-227, and a carrier selected from pharmaceutically acceptable alcohols, polyols, (poly)alkoxy derivatives, fatty acid alkyl esters, polyalkylene glycols, and dimethylsulphoxide, and a valve arranged for delivering aerosol doses of said pharmaceutical composition to the exterior of the container, wherein at least a portion of the device is formed from a polyester.

Preferably, the valve includes at least one component formed from a polyester, which component, more preferably, is a metering chamber and/or a valve core. Preferably, devices in accordance with the invention are arranged to provide metered doses of the pharmaceutically active agent included therein.

In further embodiments, the container comprises a polyester and, preferably, consists of metal lined with a polyester. The canister cap can also be so formed.

Apart from allowing the aforementioned swelling problem to be solved, an advantage of this aspect of the present invention is that use of expensive metal valve components can be avoided.

During the course of the work leading to this aspect of the present invention, tests carried out on active agent/carrier or co-solvent/HFC-134a filled metered dose aerosol devices, with acetyl copolymer or nylon valve components, showed that they failed to provide uniform doses after storage under controlled conditions. Such effects are normally associated with problems involving the gaskets or seals employed within the valve mechanisms. Thus, it came as a surprise to the applicants when they discovered that these failures were being caused by the valve components swelling to an unacceptable extent, particularly since at least one of the materials used to form them (acetyl co-polymer) was known to be stable in the presence of HFC-134a alone, or conventional active agent/carrier or co-solvent/chlorofluorocarbon formulations.

The preferred polyesters are polyalkylene benzene dicarboxylates, more preferably polyalkylene terephthalates and, most preferably, a polybutylene terephthalate.

Such materials, preferably, have a density of about 1.3 g/cm$^3$ and a water absorption of about 0.6% (23° C. saturation). The polyesters, also, are preferably partially crystalline in nature and have a crystalline melting range of 220–225° C.

Examples of suitable polybutylene terephthalates include those available under the Trademark Celanex® from Hoechst UK Limited, Walton Manner, Milton Keynes, Bucks MK7 7AJ, United Kingdom. Particularly preferred are Celanex® 2500 and Celanex® X 500/2.

Preferably, the carrier is a lower alkyl ($C_1$–$C_4$) alcohol, a polyol, or a (poly)alkoxy derivative. In embodiments, the carrier is a $C_1$–$C_4$ alkyl alcohol or a lanolin alcohol and, preferably, is ethanol or isopropyl alcohol. The most preferred alcohol is ethanol.

The preferred polyols include propylene glycol and glycerol and the preferred (poly) alkoxy derivatives include polyalkoxy alcohols, in particular 2-(2-ethoxyethoxy) ethanol (available under the Trademark Transcutol®).

Further preferred (poly)alkoxy derivatives include polyoxyalkyl ethers and esters, such as polyoxyethylene ethers or esters. The preferred polyoxyethylene ethers and esters are polyoxyethylene alkyl ethers, polyoxyethylene castor oil derivatives, polyoxyethylene sorbitan fatty acid esters and polyoxyethylene stearates.

The preferred fatty acid alkyl esters are ethyl oleate, isopropyl myristate and isopropyl palmitate. The preferred polyalkylene glycol is polyethylene glycol.

In preferred embodiments, the inventive composition can comprise up to 50% or, preferably, 25% w/w carrier. More preferred embodiments include between 3% and 15% w/w, or between 4 and 10% w/w carrier. The pharmaceutical compositions can comprise between 50% and 99% w/w, preferably between 75% and 99% w/w, and, more preferably, between 88% and 95% w/w HFC-134a or HFC-227.

In further embodiments, compositions used in the present invention can comprise a plurality of different carriers.

Further excipients can be included in the formulations employed in the present invention. For example, neutral oils as well as surfactants (the latter for aiding the smooth operation of the valve), as are well known to those skilled in the art, may be included.

Thus, in further preferred embodiments, compositions employed in the invention can comprise an organic surfactant. The preferred organic surfactant is oleyl alcohol, although others can be employed, including sorbitan trioleate, sorbitan mono-oleate, sorbitan monolaurate, polyoxyethylene (20) sorbitan monolaurate, polyoxyethylene (20) sorbitan mono-oleate, natural lecithin, oleyl polyoxytheylene (2) ether, stearyl polyoxyethylene (2) ether, lauryl polyoxyethylene (4) ether, block copolymers of oxyethylene and oxypropylene, oleic acid, synthetic lecithin, diethylene glycol dioleate, tetrahydrofurfuryl oleate, ethyl oleate, isopropyl myristate, glyceryl mono-oleate, glyceryl monostearate, glyceryl monoricinoleate, cetyl alcohol, stearyl alcohol, cetyl pyridinium chloride, olive oil, glyceryl monolaurate, corn oil, cotton seed oil or sunflower seed oil.

The pharmaceutically active agent, preferably, is insoluble, or only sparingly soluble in pure liquified HFC-134a or HFC-227. Preferably, the solubility of the active agent in liquified HFC-134a or HFC-227 is from 3 to 0.001% w/v, preferably from 1 to 0.01% w/v. However, in certain preferred embodiments, the solubility of the active agent in liquified HFC-134a or HFC-227 is from 3 to 1% w/v.

The preferred active agents include:

(1) steroid drugs such as, for example, beclomethasone, betamethasone, dexamethasone, fluticasone, hydrocortisone, budesonide, flunisolide, triamcinolone flumethasone, and prednisolone;

(2) antibiotic and antibacterial agents such as, for example, neomycin, mupirocin and chlorhexidine;

(3) systemically active drugs such as, for example, isosorbide dinitrate, isosorbide mononitrate, apomorphine and nicotine;

(4) antihistamines such as, for example, azelastine, chlorpheniramine, astemizole and terfenadine;

(5) anti-inflammatory agents such as, for example, piroxicam, nedocromil, cromoglycate, fasafungine and iodoxamide;

(6) anticholinergic agents such as, for example, ipratropium bromide and oxitroprium bromide;

(7) anti-emetics such as, for example, domperidone, hyoscine, cinnarizine metoclopramide, cyclizine, dimenhydrinate and promethazine;

(8) hormonal drugs such as, for example, vasopressin or desmopressin;

(9) bronchodilators, such as salbutamol, fenoterol and salmeterol;

(10) sympathomimetic drugs, such as tramazoline and xylometazoline;

(11) anti-fungal drugs such as miconazole;

(12) local anaesthetics such as benzocaine and lignocaine;

(13) opiates, preferably for pain management, such as buprenorphine, dextromoramide diamorphine, fentanyl, methadone, morphine, oxycodone, phenazocine, pethidine and combinations thereof with an anti-emetic;

(14) analgesics and drugs for treating migraine such as clonidine, codine, coproxamol, dextropropoxypene, ergotamine, sumatriptan, tramadol and non-steroidal anti-flammatory drugs;

(15) narcotic agonists and opiate antidotes such as naloxone, and pentazocine;

(16) phosphodiesterase type 5 inhibitors, such as sildenafil (viagra); and

(17) pharmaceutically acceptable salts of any of the foregoing.

Of these, the most preferred pharmaceutically active agent is beclomethasone dipropionate. Beclomethasone dipropionate may be employed in an anhydrous, hydrated or solvated state but, preferably, is employed in an anhydrous state. The preferred propellant is HFC-134a.

Preferably, the pharmaceutical composition includes a solution of the pharmaceutically active agent in HFC-134a or HFC-227, with the carrier as a co-solvent. It is further preferred that the co-solvent solubilises the active agent, in the sense that its presence increases the solubility of the active agent in the composition and, thus, causes or allows all or a proportion of the active agent present in the composition to dissolve and/or remain in solution.

The pharmaceutical compositions can be partial solutions in which only a proportion of the pharmaceutically active agent present therein is dissolved in the propellant and co-solvent, with the remainder being in suspension or suspendible. The exact proportions of dissolved and suspended active agent will depend upon the active agent concerned, its concentration and the identity and quantity of the co-solvent (s) used. In preferred embodiments the compositions are in the form of liquid solutions when maintained under pressure in devices in accordance with the invention.

A particularly preferred embodiment of the invention comprises a device in accordance with the first aspect of the invention filled with a solution of beclomethasone, preferably beclomethasone dipropionate, in ethanol as a co-solvent and HFC-134a as a propellant.

Devices and formulations in accordance with the invention can be used to provide sprays suitable for nasal, or sublingual administration, or for inhalation. Preferably, the compositions of this invention are formulated for administration to the nasal passages or the sublingual, mucosa and devices in accordance with the invention are arranged for providing a spray of the inventive composition to either of the latter locations.

In embodiments wherein the composition is intended for sublingual administration, it can further comprise a flavoring oil such as, for example peppermint oil Ph Eur.

In a second aspect, the invention provides the use of a polyester in contact with a composition of the type present in devices in accordance with the first aspect of the invention.

Preferably the polyester is one of those described above, and the use takes place in a metered dose dispensing aerosol device.

An embodiment of the first aspect of the present invention will now be described, by way of example only, and with reference to the following drawing.

DETAILED DESCRIPTION OF THE INVENTION

Figure 1:
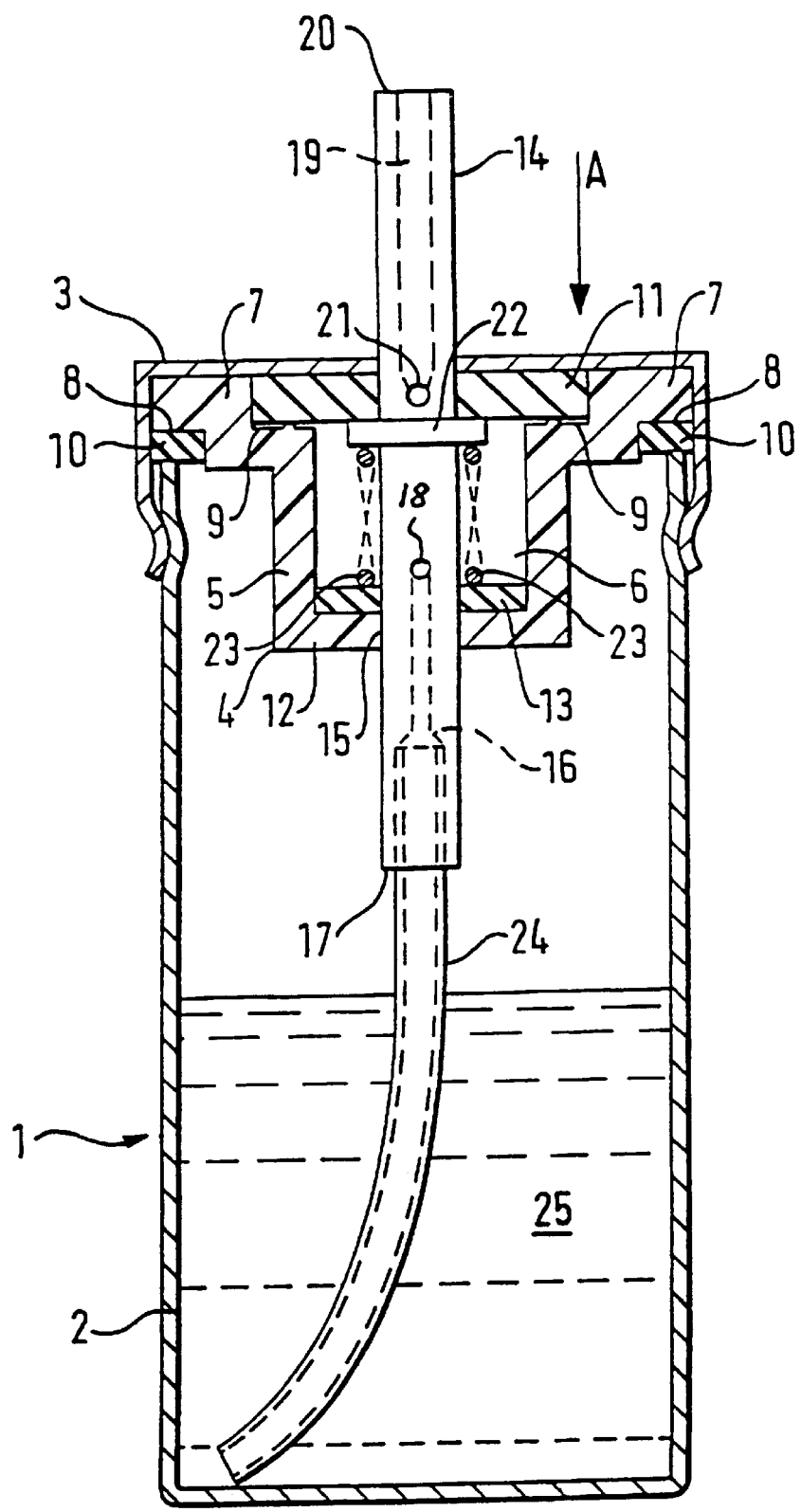
FIG. 1 is a cross sectional view of an embodiment of a device in accordance with the invention.

The device 1 comprises a substantially cylindrical canister 2 sealed with a cap 3. Both the canister 2 and the cap 3 are formed from an aluminum alloy and can be lined with a polyester (such as Celanex® 2500) or a lacquer (not shown).

A valve body moulding 4 comprises a cylindrical portion 5, which defines a metering chamber 6 and a stepped flange portion 7, and is formed by injection moulding from Celanex® 2500. The stepped flange portion 7 defines a first and outwardly facing annular seat 8 and a second, inwardly facing annular seat 9. The first annular seat 8 accommodates an annular sealing ring 10 and the second annular seat 9 accommodates a first sealing washer 11. The first sealing washer 11 is located so as to cooperate with the cylindrical portion 5 of the valve body moulding 4, in defining the metering chamber 6.

A base 12 of the cylindrical portion 5 of the valve body moulding 4 completes the boundary to the metering chamber 6 and provides a seat for a second sealing washer 13.

The sealing ring 10 and the first and second sealing washers 11 and 13 can be formed from a butyl rubber, neoprene or one of the elastomers disclosed for such purposes in WO 92/11190.

An elongate, substantially cylindrical and partially hollow valve core 14 is slidably located within the first and second sealing washers 11 and 13 and extends through an orifice 15, defined in the base 12. The valve core 14 is formed by injection moulding from Celanex® 2500.

A stepped inlet passage 16 communicates between a first end 17 of the valve core 14 and an inlet orifice 18, formed through the side of the valve core 14. In a likewise manner, an outlet passage 19 communicates between the second end 20 of the valve core 14 and an outlet orifice 21 formed through the side of the valve core 14. An annular flange 22 extends radially outwardly from the valve core 14 between the inlet and outlet orifices 18 and 21 and adjacent to the outlet orifice 21.

A stainless steel compression coil spring 23 acts between the annular flange 22 and the second sealing washer 13, urging the annular flange 22 into contact with the first sealing washer 11, such that the outlet orifice 21 lies inside the first sealing washer 11 and is thereby isolated from the metering chamber 6. In this position, as shown in FIG. 1, the inlet orifice 18 is located within the metering chamber 6. A flexible tube 24 is engaged within the stepped inlet passage 16 and extends from the valve core 14 to the base of the canister 2 (as shown in FIG. 1). Thus, the inlet orifice 18 is in communication with a region within the canister 2 adjacent to its base 12.

The cap 3 is firmly attached to the canister 2 by crimping and, thus, holds the assembly of the valve body moulding 4, valve core 14, coil spring 23, sealing washers 11 and 13 and sealing ring 10 in place as shown in FIG. 1, with the sealing ring 10 and first sealing washer 11 sufficiently compressed to seal the interior of the device 1 and prevent the egress of its contents. Downward movement of the valve core, in the direction of arrow A, against the action of the spring 22 will bring the outlet orifice 21 into the metering chamber immediately after the first orifice 18 has been sealed from the metering chamber 6 by the second sealing washer 13.

When filled with a composition in accordance with the present invention, as shown at 25, the device 1 will provide metered doses of the composition when used as follows. The device 1 should be held in the position shown in FIG. 1, so that the composition 25, by virtue of its pressure, enters the metering chamber 6 via the tube 24, the inlet passage 16 and the inlet orifice 18. Subsequent depression of the valve core 14, in the direction of arrow A, seals the inlet orifice 18 and hence the remainder of the canister 2, from the metering chamber 6 and opens the outlet passage to the metering chamber 6, via the outlet orifice 21. Since the composition 25 in the metering chamber 6 is pressurized with the propellant, it will be expelled from the metering chamber 6 through the outlet orifice 21 and the outlet passage 19. If the valve core 14 is then allowed to return to the position shown in FIG. 1, under the influence of the spring 22, the outlet orifice 21 is again sealed from the metering chamber 6 and the metering chamber 6 will be filled with pressurized composition 25 from the canister 2, via the tube 24, stepped inlet passage 16 and inlet orifice 18.

EXAMPLE 1

A composition comprising beclomethasone dipropionate (BDP) with HFC- 134a suitable for use in a device as described above was formulated from the following ingredients:

| Component | percent w/w | g/can |
| --- | --- | --- |
| BDP (anhydrous) | 0.164 | 0.010 |
| Ethanol 96% BP | 4.992 | 0.305 |
| HFC-134a | 94.844 | 5.795 |
| Total | 100 | 6.11 |

The BDP was dissolved in the ethanol in the proportions set out above and 0.315 g of the resulting solution was then placed in a canister 2 and a valve assembly, comprising a valve body moulding 4, first sealing washer 11, second sealing washer 13, spring 22, tube 23, and annular seal 10, was then sealed onto the canister 2 by crimping as shown in FIG. 1 by the cap 3. The propellant (HFC-134a) was then added to the canister, by being forced through the valve core 14 at great pressure, and the complete device was then checked for leaks. After the propellant entered the canister it dissolved the remaining portions of the composition.

In a preferred embodiment, each expelled dose of the above formulation is of approximately 25 µl and provides 50 µg of BDP.

EXAMPLE 2

A second composition comprising BDP and suitable for use in a device as described above was formulated from the following ingredients:

| Component | percent w/w | g/can |
| --- | --- | --- |
| BDP (anhydrous) | 0.164 | 0.010 |
| Ethanol 96% BP | 7.5 | 0.458 |
| HFC-134a | 92.336 | 5.641 |
| Total | 100 | 6.11 |

The BDP was dissolved in the ethanol in the proportions set out above and 0.315 g of the resulting solution was then placed in a canister 2. A valve assembly (as described in Example 1) was than sealed onto the canister 2 by crimping and the HFC-134a propellant was then added to the canister, by being forced through the valve core 14 at great pressure, and the complete device was then checked for leaks. After the propellant entered the canister it dissolved the remaining portions of the composition.

In a preferred embodiment, each expelled dose of the above formulation is approximately 25 μl and provides 50 μl of BDP.

EXAMPLE 3

Further compositions comprising BDP with HFC-134a, suitable for use in a device as described herein, were formulated in accordance with the details set out in the following table, in which all figures are given on a percent by weight basis.

| Formulation | A | B | C | D | E |
|---|---|---|---|---|---|
| BDP | 0.164 | 0.164 | 0.164 | 0.164 | 0.164 |
| Transcatol | 9.984 | 4.992 | | | |
| Oleyl alcohol | | | 2.496 | | |
| Propylene glycol | | | | 4.992 | |
| Ethanol | | 4.992 | 7.488 | 4.992 | 20.51 |
| p134a | 89.852 | 89.852 | 89.852 | 89.852 | 79.326 |
| Total | 100 | 100 | 100 | 100 | 100 |

Formulations A–E are prepared using a similar technique to that set out in Example 1 above. Briefly, the BDP is dissolved with the other excipient or excipients (excepting the HFC-134a) and the resulting solution is then placed in a canister 2. A valve assembly is then sealed onto the canister 2 by crimping and the HFC-134a propellant is then added to the canister 2, by being forced through the valve core 14 at great pressure. After the propellant enters the canister 2, it dissolves the remaining portions of each composition.

Although only BDP is referred to in this example, other ones of the active agents previously discussed in this application may be substituted therefor in quantities which would dissolve at least partially in the propellant/co-solvent mixture.

EXAMPLES 4–13

Eight further compositions suitable for use in a device as described herein, were formulated in accordance with the details set out in the following table.

| Example | Component | Percent w/w |
|---|---|---|
| EXAMPLE 4 | Mupirocin | 0.1 |
| | Tween 20 | 0.1 |
| | Ethanol | 20.0 |
| | HFC-134a | 79.8 |
| EXAMPLE 5 | Isosorbide Dinitrate | 1.0 |
| | Propylene Glycol | 3.0 |
| | Peppermint Oil Ph Eur | 1.0 |
| | Ethanol | 15.0 |
| | HFC-134a | 80.0 |
| EXAMPLE 6 | Cromoglycate | 0.2 |
| | Span 5 | 0.1 |
| | Ethanol | 20.0 |
| | HFC-134a | 79.7 |
| EXAMPLE 7 | Domperidone | 0.2 |

-continued

| Example | Component | Percent w/w |
|---|---|---|
| | Oleyl alcohol | 0.1 |
| | Transcutol | 4.0 |
| | Ethanol | 10.0 |
| | HFC-134a | 84.7 |
| EXAMPLE 8 | Salbutamol | 0.2 |
| | Oleic acid | 0.01 |
| | Miglyol 840 | 2.0 |
| | Ethanol | 10.0 |
| | HFC-134a | 87.89 |
| EXAMPLE 9 | Xylometazoline | 0.1 |
| | Oleic acid | 0.01 |
| | Propylene glycol | 3.0 |
| | Ethanol | 12.0 |
| | HFC-134a | 84.89 |
| EXAMPLE 10 | Miconazole | 1.0 |
| | Oleic acid | 0.1 |
| | Transcutol | 4.0 |
| | Ethanol | 16.0 |
| | HFC-134a | 78.9 |
| EXAMPLE 11 | Benzocaine | 1.0 |
| | PEG 400 | 4.0 |
| | Ethanol | 5.0 |
| | HFC-134a | 90.0 |
| EXAMPLE 12 | Fentanyl | 0.1 |
| | Oleyl alcohol | 0.1 |
| | Ethanol | 15.0 |
| | HFC-227 | 20.0 |
| | HFC-134a | 64.3 |
| | Peppermint oil | 0.5 |
| EXAMPLE 13 | Naloxone | 0.1 |
| | Oleic acid | 0.1 |
| | Ethanol | 15.0 |
| | HFC-227 | 15.0 |
| | HFC-134a | 69.3 |
| | Peppermint oil | 0.5 |

These compositions are prepared using a similar technique to that set out in Examples 1–2. Briefly, the active agent is mixed with the other excipient or excipients (excepting the 1HFC-134a and the HFC-227 if used) and the resulting solution and/or suspension is then placed in a canister 2. A valve assembly (as described in Example 1) is then sealed onto the canister 2 by crimping and the HFC-134a and HFC-227 (if used) propellant is then added to the canister, by being forced through the valve core 14 at great pressure. After the propellant enters the canister 2, it at least partially and in some cases completely dissolves the remaining portions of each composition.

What is claimed is:

1. A device for providing pharmaceutical doses comprising
   a container filled with a pharmaceutical composition including a pharmaceutically active agent in a solution of liquefied 1,1,1,2-tetrafluoroethane (HFC-134a), or 1,1,1,2,3,3,3-heptafluoropropane (HFC-227), and a carrier selected from the group consisting of pharmaceutically acceptable alcohols, polyols, (poly) alkoxys, fatty acid alkyl esters, polyalkylene glycols, and dimethyl sulphoxide, and
   a valve arranged for delivering aerosol doses of said pharmaceutical composition to the exterior of the container, wherein all components of the valve are formed from a polyester.

2. A device as claimed in claim 1 wherein the carrier is a $C_1$–$C_4$ lower alkyl alcohol on a lanolin alcohol.

3. A device as claimed in claim 2 wherein the carrier is ethanol or isopropyl alcohol.

4. A device as claimed in claim 3 wherein the carrier is ethanol.

5. A device as claimed in claim 1 wherein the carrier is propylene glycol or glycerol.

6. A device as claimed in claim 1 wherein the carrier is a polyalkoxy alcohol.

7. A device as claimed in claim 6 wherein the carrier is 2-(2-ethoxy ethoxy) ethanol.

8. A device as claimed in claim 1 wherein the carrier is a polyoxyalkyl ether or ester.

9. A device as claimed in claim 8 wherein the carrier is a polyoxyethylene ether or ester.

10. A device as claimed in claim 9 wherein the carrier is selected from the group consisting of polyoxyethylene alkyl ether, a polyoxyethylene caster oil, a polyoxyethylene sorbitan fatty acid ester and a polyoxyethylene stearate.

11. A device as claimed in claim 1 wherein the carrier is selected from the group consisting of ethyl oleate, isopropyl myristate and isopropyl palmitate.

12. A device as claimed in claim 1 wherein the carrier is polyethylene glycol.

13. A device as claimed in claim 1 wherein the composition comprises up to 50% w/w of carrier.

14. A device as claimed in claim 13 wherein the composition comprises up to 25% w/w of carrier.

15. A device as claimed in claim 1 wherein the composition comprises from about 50% to about 99% w/w of HFC-134a or HFC-227.

16. A device as claimed in claim 1 wherein the composition comprises from about 75% to about 95% w/w of HFC-134a or HFC-227.

17. A device as claimed in claim 1 wherein the composition comprises a plurality of carriers.

18. A device as claimed in claim 1 wherein the composition further comprises an organic surfactant.

19. A device as claimed in claim 18 wherein the organic surfactant is selected from the group consisting of oleyl alcohol, sorbitan trioleate, sorbitan mono-oleate, sorbitan monolaurate, polyoxyethylene (21) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, oleic acid, synthetic lecithin, diethylene glycol dioleate, tetrahydrofurfuryl oleate, ethyl oleate, isopropyl myristate, glyceryl mono-oleate, glyceryl monostearate, glyceryl monoricinoleate, cetyl alchololol, stearyl alcohol, cetyl pyridinium chloride, olive oil, glyceryl monolaurate, corn oil, cotton seed oil, and sunflower oil.

20. A device as claimed in claim 18 wherein the surfactant is oleyl alcohol.

21. A device as claimed in claim 1 wherein the pharmaceutically active agent is insoluble in liquified HFC-134a or HFC-227.

22. A device as claimed in claim 1 wherein the pharmaceutically active agent is sparingly soluble in liquified HFC-134a or HFC-227.

23. A device as claimed in claim 1 wherein the pharmaceutically active agent is selected from the group consisting of steroid drugs, antibiotic and antibacterial agents, systemically active drugs, antihistamines, anti-inflammatory agents, anticholinergic agents, anti-emetics, hormonal drugs, bronchodilators, sympathomimetic drugs, anti-fungal drugs, local anaesthetics, and pharmaceutically acceptable salts of the foregoing.

24. The device as claimed in claim 23 wherein the steroid drug is selected from the group consisting of beclomethasone, betamethasone, dexamethasone, fluticasone, hydrocortisone, budesonide, flunisolide, triamcinolone flumethasone and prednisolone.

25. The device as claimed in claim 23 wherein the antibiotic and antibacterial agent is selected from the group consisting of neomycin, mupirocin, and chlorhexidine.

26. The device as claimed in claim 23 wherein the systemically active drug is selected from the group consisting of isosorbide dinitrate, isosorbide mononitrate, apomorphine, and nicotine.

27. The device as claimed in claim 23 wherein the antihistamine is selected from the group consisting of azelastine, chlorpheniramine, astemizole and terfenadine.

28. The device as claimed in claim 23 wherein the anti-inflammatory agent is selected from the group consisting of piroxicam, nedocromil, cromoglycate, fasafungine and iodoxamide.

29. The device as claimed in claim 23 wherein the anticholinergic agent is ipratropium bromide or oxitroprium bromide.

30. The device as claimed in claim 23 wherein the anti-emetic is selected from the group consisting of domperidone, hyoscine, cinnarizine metoclopramide, cyclizine, dimenhydrinate and promethazine.

31. The device as claimed in claim 23 wherein the hormonal drug is vasopressin or desmopressin.

32. The device as claimed in claim 23 wherein the bronchodilator is selected form the group consisting of salbutamol, fenoterol and salmeterol.

33. The device as claimed in claim 23 wherein the sympathomimetic drug is tramazoline or xylometazoline.

34. The device as claimed in claim 23 wherein the anti-fungal drug is miconazole.

35. The device as claimed in claim 23 wherein the local anaesthetic is benzocaine or lignocaine.

36. A device as claimed in claim 1 wherein the pharmaceutically active agent is selected from the group consisting of opiates, analgesics and drugs for treating migrane, narcotic agonists and opiate antidotes, phosphodiesterase type 5 inhibitors, and pharmaceutically acceptable salts of the foregoing.

37. The device as claimed 35 wherein the opiate is for pain management and is selected from the group consisting of buprenorphine, dextromoramide, diamorphine, fentanyl, methadone, morphine, oxycodone, phenazocine, pethidine, and mixtures thereof with an anti-emetic.

38. The device as claimed in claim 35 wherein the analgesics and drugs for treating migraine are selected from the group consisting of clonidine, codine, coproxamol, dextropropoxypene, ergotamine, sumatriptan, tramadol, and non-steroidal anti-inflammatory drugs.

39. The device as claimed in claim 35 wherein the narcotic agonist and opiate antidote is naloxone and pentazocine.

40. The device as claimed in claim 35 wherein the phosphodiesterase type 5 inhibitor is sildenafil.

41. A device as claimed in claim 1 wherein the pharmaceutically active agent is beclomethasone dipropionate.

42. A device as claimed in claim 41 wherein the beclomethasone dipropionate is in an anhydrous, hydrated or solvated state.

43. A device as claimed in claim 1 wherein the composition comprises HFC-134a as a propellant.

44. A device as claimed in claim 1 which is substantially free of weak organic or strong inorganic acids.

45. A device as claimed in claim 1 wherein the solubility of the active agent in liquified HFC-134a or HFC-227 is from about 0.001% to about 3% w/v.

46. A device as claimed in claim 45 wherein the solubility of the active agent in liquified HFC-134a or HFC-227 is from about 0.01% to about 1% w/v.

47. A device as claimed in claim 1 wherein said container includes a canister body comprising a polyester.

48. A device as claimed in claim 47 wherein the canister body is formed from metal lined with a polyester.

49. A device as claimed in claim 1 wherein the device includes a canister cap or lining formed from a polyester.

50. A device as claimed in claim 1 wherein the polyester is a polyalkylene benzene dicarboxylate.

51. A device as claimed in claim 50 wherein the polyester is polyalkylene terephthalate.

52. A device as claimed in claim 51 wherein the polyester is polybutylene terephthalate.

53. A device as claimed in claim 1 wherein the composition further comprises a flavouring oil.

54. The device as claimed in claim 53 wherein the flavoring oil is peppermint oil.

55. A device as claimed in claim 1 wherein the pharmaceutical composition includes a solution of the pharmaceutically active agent in liquified HFC-134a or HFC-227, with the carrier as a co-solvent.

56. A device as claimed in claim 55 wherein the co-solvent solubilizes the pharmaceutically active agent.

57. A device as claimed in claims 55 or 56 wherein substantially all of the pharmaceutically active agent present in the pharmaceutical composition is dissolved in the propellant and co-solvent.

58. A device as claimed in claim 1 wherein a proportion of the pharmacuetically active agent present in the pharmaceutical compostion is dissolved in the propellant and co-solvent, with the remainder being in suspension.

59. A device as claimed in claim 1 wherein the composition comprises HFC-134a, beclamethasone dipropionate and ethanol.

* * * * *